(12) United States Patent
van't Hooft

(10) Patent No.: US 7,648,453 B2
(45) Date of Patent: Jan. 19, 2010

(54) CATHETER NEEDLE FOR INTERNALLY IRRADIATING A TUMOR IN A BODY PART

(75) Inventor: Eric van't Hooft, Brasschaat (BE)

(73) Assignee: Isodose Control Intellectual Property B.V., Veenendal (NL)

( * ) Notice: Subject to any disclaimer, the term of this patent is extended or adjusted under 35 U.S.C. 154(b) by 124 days.

(21) Appl. No.: 11/485,755

(22) Filed: Jul. 13, 2006

(65) Prior Publication Data

US 2007/0265486 A1 Nov. 15, 2007

(30) Foreign Application Priority Data

May 10, 2006 (NL) .................................. 1031786

(51) Int. Cl.
*A61N 5/00* (2006.01)
(52) U.S. Cl. ......................................................... 600/7
(58) Field of Classification Search ...................... 600/1, 600/3, 6, 7, 8; 604/27, 173, 192, 198, 218, 604/57; 414/146; 606/185; 250/516.1
See application file for complete search history.

(56) References Cited

U.S. PATENT DOCUMENTS

| | | | | |
|---|---|---|---|---|
| 1,442,051 A | * | 1/1923 | Cummings | 600/8 |
| 1,494,826 A | * | 5/1924 | Viol | 600/8 |
| 1,565,490 A | * | 12/1925 | Muguet | 600/8 |
| 1,578,945 A | * | 3/1926 | Withers | 600/8 |
| 2,512,569 A | * | 6/1950 | Saffir | 604/272 |
| 3,762,243 A | * | 10/1973 | Borrkfield | 205/122 |
| 3,952,742 A | | 4/1976 | Taylor | |
| 4,592,356 A | * | 6/1986 | Gutierrez | 606/185 |
| 4,790,817 A | | 12/1988 | Luther | |
| 4,976,680 A | * | 12/1990 | Hayman et al. | 600/7 |
| 5,171,226 A | * | 12/1992 | McCrory | 604/164.01 |
| 5,569,213 A | | 10/1996 | Humphrey | |
| 6,554,760 B2 | * | 4/2003 | Lamoureux et al. | 600/7 |
| 7,104,945 B2 | * | 9/2006 | Miller | 600/7 |
| 2003/0135153 A1 | * | 7/2003 | Hagemeier | 604/59 |
| 2004/0133254 A1 | | 7/2004 | Sterzer et al. | |
| 2005/0070753 A1 | * | 3/2005 | Forman et al. | 600/3 |

FOREIGN PATENT DOCUMENTS

WO  WO 93/25155 A1  12/1993
WO  WO 2004/030740 A1  4/2004

* cited by examiner

*Primary Examiner*—Samuel G Gilbert
(74) *Attorney, Agent, or Firm*—Leydig, Voit & Mayer, Ltd

(57) ABSTRACT

A catheter needle, for irradiating tumors, formed by an elongated plastic tube with parts partly unfoldable outwards which can lock themselves in the tissue, and a closed end. The closed end has a reinforced sharp pointed shape with which tissue can be punctured. In the improved version, therefore, a point from a harder material is provided which is provided in or around the plastic so that the catheter needle has sufficient sharpness like a conventional metal needle. Thus, the catheter needle can puncture the skin and harder, deeper-lying tissues directly without pre-puncturing or other aids.

7 Claims, 3 Drawing Sheets

CATHETER NEEDLE FOR INTERNALLY IRRADIATING A TUMOR IN A BODY PART

BACKGROUND OF THE INVENTION

The invention relates to a catheter needle for internally radiating a tumor in a body part.

BACKGROUND OF THE INVENTION

In some therapeutic treatments, in particular irradiating patients for the treatment of tumors, it is necessary to provide a plurality of catheters in the tissue. In the treatment of prostate tumors in men, for instance, it is common practice to pre-puncture the patient's skin with a sharp metal point before plastic needles are inserted in the prostate. In these needles, at a later time, radioactive sources are positioned in the catheters for irradiating a tumor located in the needles' vicinity without overloading the surrounding tissue. For the patient, a treatment with such a plastic needle is extremely traumatic, due to the blunt point being pressed through the usually harder tissue with force which is very painful. Due to the degree of pain normally experienced complete anesthesia is often required. Further, pressing a blunt needle with great force can result in wound fluid formation.

BRIEF SUMMARY OF THE INVENTION

It is an object of the invention to provide an alternative to the above-mentioned treatment method and, to this end, the invention provides an apparatus according to claim 1. In particular, the invention provides a catheter needle which is shaped as an elongated tube of a first material with a closed end, and a sharp point from a second material which is harder than the first material.

BRIEF DESCRIPTION OF THE SEVERAL VIEWS OF THE DRAWINGS

The invention will now be explained in more detail with reference to the description of the Figures, in which.

DETAILED DESCRIPTION OF THE DRAWINGS

Figure 1:
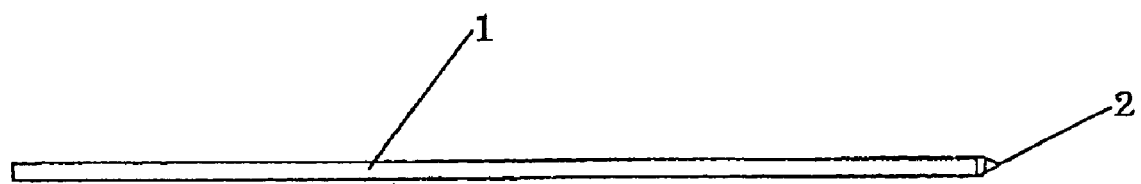
FIG. 1 shows a conventional catheter.

FIG. 1 shows a conventional catheter 1. The catheter 1 contains a conventional catheter needle 2 which is fed through the catheter 1. The needle 2 can be inserted into the tissue with catheter 1. After providing the needle 2 in the tissue, the needle 2 is removed from the catheter 1 by, for instance, withdrawing it at the back side, and the catheter 1 can be connected to a brachytherapy apparatus (not shown). The brachytherapy apparatus feeds a radioactive source through the catheter 1 to the position to be irradiated in the tissue. Conventional brachytherapy provides the placement of a number of catheters in a tissue to be irradiated in predetermined positions such that the tissue receives a predetermined irradiation dose from radioactive sources which are provided in the catheters.

Figure 2:
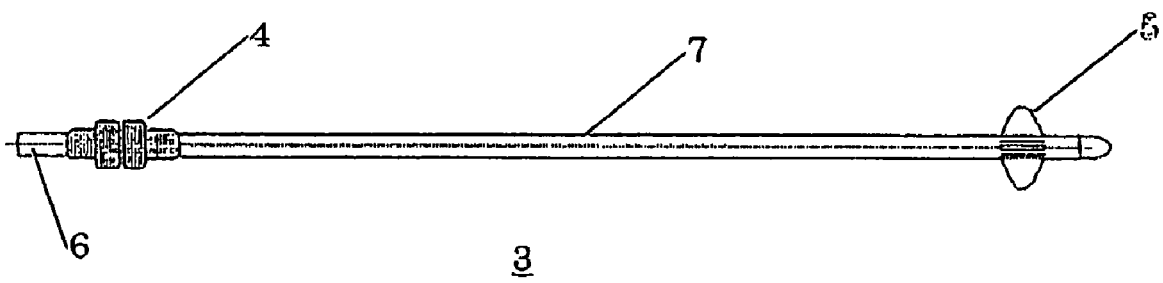
FIG. 2 shows a conventional anchoring needle.

FIG. 2 shows a conventional anchoring needle 3 which can be used for fixation in a tissue. Such anchoring needles known per se typically have an anchoring mechanism for anchoring in the tissue. Typically, such needles include a double wall of which the outer wall has multiple parallel indentations all round so that, upon pulling an inner catheter, the outer wall bends outwards at the location of the indentations so that the catheter locks in the tissue. The anchoring needle 3 typically comprises a fixing part 4 and a laterally movable anchoring element 5 to be anchored in the body part. The laterally movable anchoring element 5 can be fixed by rotation or displacement of the fixing part. This may, for instance, be achieved by means of a central part 6, which can be moved in a tube part 7 and which presses the anchoring element 5, formed by a strip-shaped structure provided in the tube part, laterally outwards upon displacement. FIG. 2 shows the position pressed outwards of the anchoring element 5.

Figure 3:
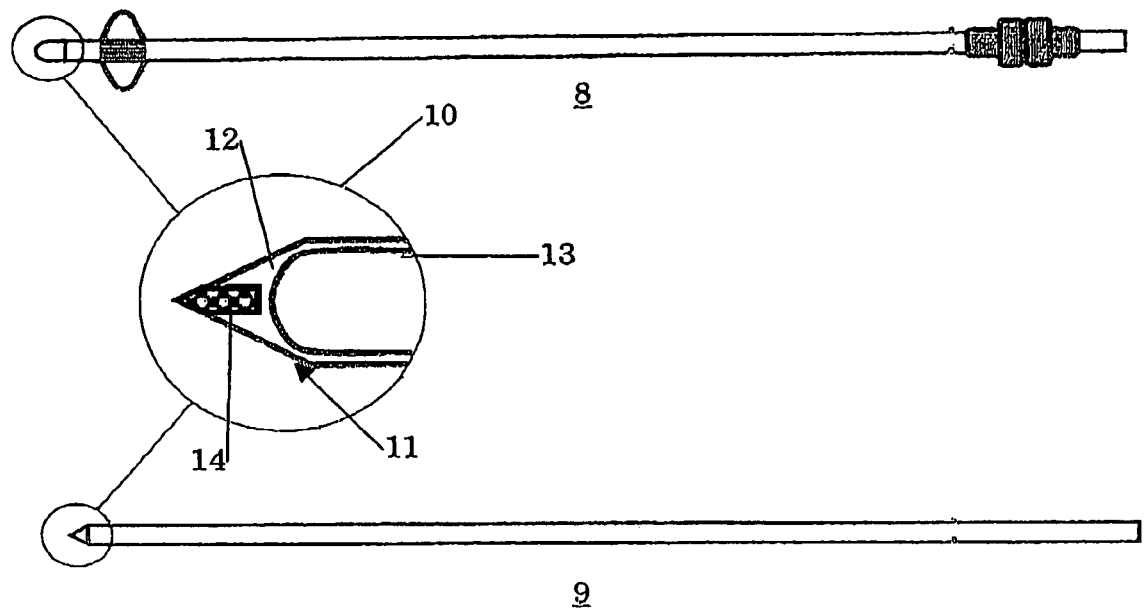
FIG. 3 shows an embodiment of the apparatus according to the invention.

FIG. 3 shows the catheter needle 8 and 9, respectively, according to the invention. In particular, the detailed view 10 shows end 11 of catheter needle 8 with anchoring and of catheter needle 9 without anchoring. End 11 is formed by a closed end 12 of a hollow guide tube 13. The tube material is a plastic. In the closed end 12, a sharp point 14 is placed. The sharp point 14 is made, for example, from a metal or ceramic material. As an example, titanium metal is used for the sharp point 14. Plastic points 14 have the property that they do not have the same sharpness as metal or ceramic points. The invention solves this problem by placing a sharp point 14 from a hard material in the plastic end 12 of the catheter tube 8 and 9, respectively. Thus, the catheter tube 8 and 9, respectively, has the same sharpness as a completely metal needle. Thus, the catheter tube 8 and 9, respectively, can puncture the skin directly, without pre-puncturing or other aids, and can be inserted into tissues difficult to penetrate for plastic needles, such as a prostate gland.

Figure 4:
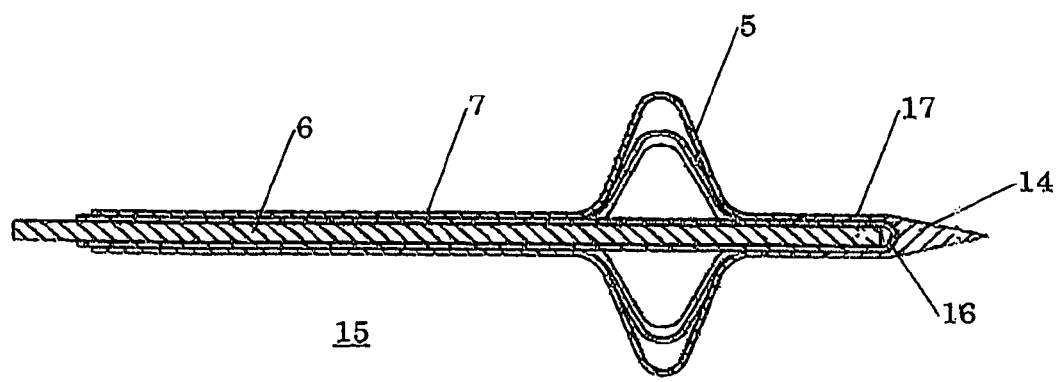
FIG. 4 shows an alternative embodiment of the apparatus according to the invention.

FIG. 4 shows a further embodiment according to the invention. Although the embodiment is shown as a locking needle 15 with an anchoring element 5 folding outwards, the principle according to the invention can of course also be applied to non-locking variants. FIG. 4 shows an inner tube 6 and an outer tube 7 movable around it, which are glued together near end 16 around which a sleeve-shaped element 17 is cased as a connecting element, which tapers on the front side, i.e. the side facing away from the catheter needle, into a sharp point 14. The sleeve-shaped element 17 is designed with a sharp needle and made of, for example, titanium. Other suitable materials may of course be used as well. Another variant may be a separate (sleeve-shaped) casing element or connecting element, which forms a connection between a (separate) point and the end of the catheter needle.

Figure 5:
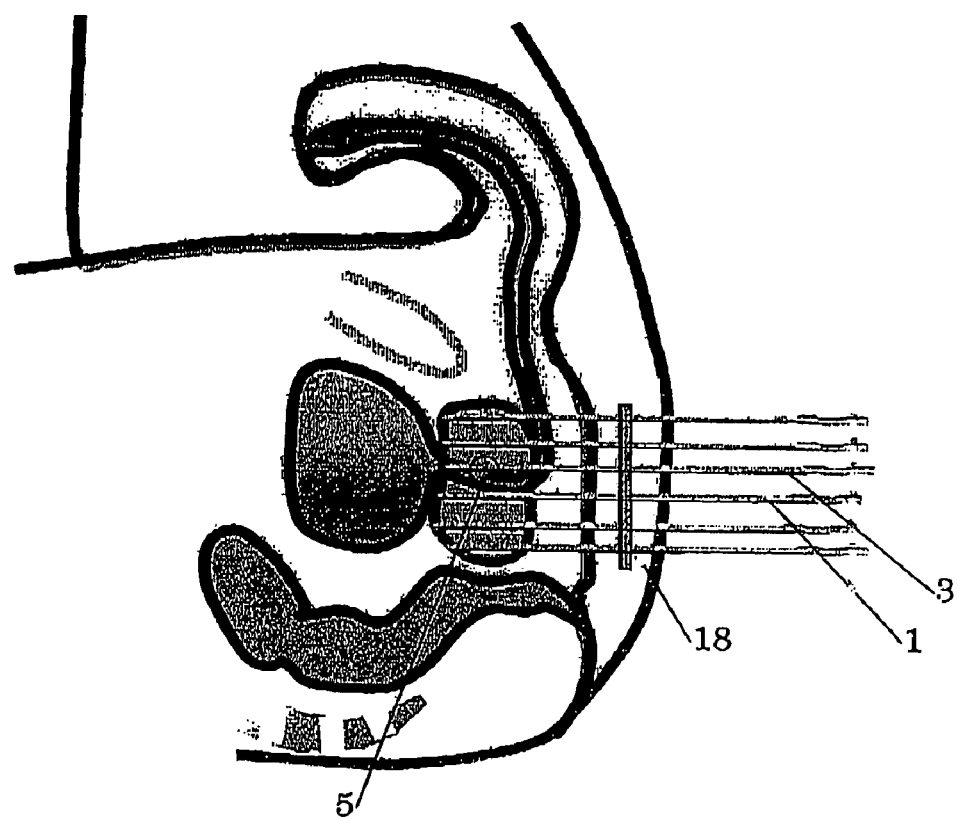
FIG. 5 shows a side elevational view of the apparatus in use.

FIG. 5 shows a schematic view of the catheter needle in use. The catheter needle 1 may be anchored to a template 18. The template 18 serves to aid positioning the catheter needles 1 and 3. Some catheter needles 3 may involve the embodiment 3 with anchoring element 5 discussed with reference to FIG. 2. Both catheter needles 1 and 3 may be suitable for use as a guide tube for guiding a radioactive source (not shown).

The invention is not limited to the embodiments shown in the drawing, but may also comprise alternatives or variants thereof which fall within the scope of the following claims. Such variants are understood to fall within the claims defined as follows.

What is claimed is:

1. An anchoring catheter needle for internally irradiating a tumor in a body part, wherein the catheter needle comprises an elongated tube from a first material, characterized in that the needle further comprises an inner tube with closed end piece, the tube comprising a strip shaped anchoring structure that is laterally movable relative to the inner tube, the inner tube and outer tube being connected near the closed end by a casing element having a sharp point that is formed from a second material which is harder than the first material.

2. A catheter needle according to claim 1, characterized in that the first material is a plastic.

3. A catheter needle according to claim 1, characterized in that the sharp point is from metal.

4. A catheter needle according to claim 1, characterized in that the sharp point is from titanium.

5. A catheter needle according to claim 1, characterized in that the sharp point is from a hard plastic.

6. A catheter needle according to claim 1, characterized in that the sharp point is from ceramic material.

7. A catheter needle according to claim 1, characterized in that the sharp point is cased in the first material.

* * * * *

UNITED STATES PATENT AND TRADEMARK OFFICE
CERTIFICATE OF CORRECTION

PATENT NO. : 7,648,453 B2
APPLICATION NO. : 11/485755
DATED : January 19, 2010
INVENTOR(S) : Eric van't Hooft Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 17 days.

Signed and Sealed this

Twenty-eighth Day of December, 2010

David J. Kappos
*Director of the United States Patent and Trademark Office*